(12) United States Patent
Wales et al.

(10) Patent No.: US 11,090,353 B2
(45) Date of Patent: Aug. 17, 2021

(54) GLUTEN-FREE GRAIN-CONCENTRATE SUBSTITUTE FOR FERMENTED WHEAT GERM DRUG PRODUCT AND METHOD PREPARATION

(71) Applicants: David Wales, Stanford, CT (US); Michael F. Javes, Hartland, WI (US); Gyula Bencze, Huntington Station, NY (US)

(72) Inventors: David Wales, Stanford, CT (US); Michael F. Javes, Hartland, WI (US); Gyula Bencze, Huntington Station, NY (US)

( * ) Notice: Subject to any disclaimer, the term of this patent is extended or adjusted under 35 U.S.C. 154(b) by 113 days.

(21) Appl. No.: 16/501,566

(22) Filed: Apr. 29, 2019

(65) Prior Publication Data

US 2019/0282651 A1    Sep. 19, 2019

Related U.S. Application Data (63) Continuation-in-part of application No. 15/731,040, filed on Apr. 10, 2017, now abandoned, which is a continuation-in-part of application No. 14/545,753, filed on Jun. 15, 2015, now abandoned, which is a continuation-in-part of application No. 14/545,361, filed on Apr. 27, 2015, now abandoned, which is a
(Continued)

(51) Int. Cl.
| | |
|---|---|
| *A61K 36/899* | (2006.01) |
| *A23L 7/25* | (2016.01) |
| *A61K 47/38* | (2006.01) |
| *A61K 31/122* | (2006.01) |

(52) U.S. Cl.
CPC .............. *A61K 36/899* (2013.01); *A23L 7/25* (2016.08); *A61K 31/122* (2013.01); *A61K 47/38* (2013.01); *A23V 2002/00* (2013.01); *A23V 2200/3202* (2013.01); *A23V 2250/51084* (2013.01); *A23V 2250/51086* (2013.01); *A23V 2250/5486* (2013.01); *A61K 2236/19* (2013.01); *A61K 2236/30* (2013.01)

(58) Field of Classification Search
CPC ....... A23K 36/899; A23L 7/25; A61K 31/122; A61K 36/899; A61K 47/38; A61K 2236/19; A61K 2236/30
USPC ........................................................ 426/61
See application file for complete search history.

(56) References Cited

U.S. PATENT DOCUMENTS

| | | | |
|---|---|---|---|
| 2,085,421 A | 6/1937 | Donk et al. | |
| 4,024,120 A * | 5/1977 | Phillips | A23J 1/12 530/374 |
| 4,057,654 A | 11/1977 | Smith et al. | |

(Continued)

OTHER PUBLICATIONS

Yusuf, O. K. et al. J. Med. Plants Res. 4: 2016-2020 (Year: 2010).*

(Continued)

*Primary Examiner* — Hamid R Badr (57) ABSTRACT

A gluten-free grain concentrate (GFGC) drug product and stepwise process to prepare GFGC from the treatment of raw unground wheat germ, is provided resulting in a product having at least three active components including (a) 1% to 3% 2,6-dimethoxy-1,4-hydroquinone; (b) 2% to 4% monomethoxy-1,4-benzoquinone; and (c) 0.5% to 1.5% monomethoxy-1,4-hydroquinone; and at least one inactive component: 2,6 dimethyl benzoquinone.

2 Claims, 4 Drawing Sheets

| | Gluten (ppm) | Color | Density gm/cm3 | pH of water solution | Appearance | Odor | Taste |
|---|---|---|---|---|---|---|---|
| Present Invention with inert elements | 0.00 - 0.6 | Light brown | 0.6 | 4.6 | Light powder | Acidic | Bitter |
| Present invention with inert elements removed | 0.00 - 0.6 | Red | 1.07 | <1 | Thick liquid | Acidic | No data |
| Hidvégi A 250 product | 75 | Dark brown | 0.7 | 4-5.2 | Coarse powder | Sweet (chocolate like) | Slightly bitter |
| Hidvégi product treated with ethyl acetate to remove gluten | 18 | Dark red | 0.96 | 4 | Paste / chunks | Fruit smell | Bitter |

Related U.S. Application Data continuation-in-part of application No. 13/998,808, filed on Dec. 9, 2013, now abandoned.

(60) Provisional application No. 61/854,336, filed on Apr. 22, 2013.

(56) References Cited

U.S. PATENT DOCUMENTS

| | | | |
|---|---|---|---|
| 4,379,028 | A | 4/1983 | Berg et al. |
| 5,063,079 | A | 11/1991 | Ferrera et al. |
| 6,355,474 | B1 | 3/2002 | Hidvégi et al. |
| 8,563,050 | B2 | 10/2013 | Hidvégi |
| 2010/0323045 | A1* | 12/2010 | Pischel .................... A61P 1/04 424/767 |
| 2012/0164132 | A1 | 6/2012 | Hidvégi et al. |

OTHER PUBLICATIONS

Cosgrove, D. J. et al. Nature; 169: 966-967 (Year: 1952).*
Yusuf, Oluwatosin K. et al., "Studies of phytochemical constituents and anti-trypanosomal properties . . . " Journal of Medicinal Plants Research (Oct. 4, 2010): 2016-2020.
Row, KH, et al., "Recovery of catechin compounds from Korean tea by solvent extraction," Bioresour Techno. Mar. 2006;97(5):790-3.
Christoph Otto, et al., Antiproliferative and antimetabolic effects behind the anticancer . . . (BMC Compl. & Alt. Med) (Jun. 1, 2016) 16:160•, DOI: 10.1186//s12906-016-1138-5).
Riley, PA, "Free Radicals in Biology: Oxidative Stress and the Effects of Ionizing Radiation", Int'l J. Radiation Biology, vol. 65, Issue 1, 1994.

* cited by examiner

| | Gluten (ppm) | Color | Density gm / cm3 | pH of water solution | Appearance | Odor | Taste |
|---|---|---|---|---|---|---|---|
| Present Invention with inert elements | 0.00 - 0.6 | Light brown | 0.6 | 4.6 | Light powder | Acidic | Bitter |
| Present invention with inert elements removed | 0.00 - 0.6 | Red | 1.07 | <1 | Thick liquid | Acidic | No data |
| Hidvégi A 250 product | 75 | Dark brown | 0.7 | 4-5.2 | Coarse powder | Sweet (chocolate like) | Slightly bitter |
| Hidvégi product treated with ethyl acetate to remove gluten | 18 | Dark red | 0.96 | 4 | Paste / chunks | Fruit smell | Bitter |

GLUTEN-FREE GRAIN-CONCENTRATE SUBSTITUTE FOR FERMENTED WHEAT GERM DRUG PRODUCT AND METHOD PREPARATION

CROSS-REFERENCE(S)

This is a continuation-in-part application (CIP), claiming the benefit of priority to CIP application Ser. No. 15/731,040 filed Apr. 10, 2017 (10 Apr. 2017), which in turn claims priority to CIP Ser. No. 14/545,753 filed Jun. 15, 2015 (15 Jun. 2015), claiming priority to CIP Ser. No. 14/545,361 filed Apr. 27, 2015 (27 Apr. 2015), claiming priority to CIP Ser. No. 13/998,808 filed Dec. 9, 2013 (9 Dec. 2013), and claiming priority to provisional patent application Ser. No. 61/854,336 filed Apr. 22, 2013 (22 Apr. 2013).

BACKGROUND OF THE INVENTION

Field of the Invention

The present disclosure relates to the field of drugs made from wheat and a method of making a gluten-free wheat-based drug product. More particularly, the present invention discloses a product with at least three active components including (a) 2,6-dimethoxy-1,4-hydroquinone; (b) monomethoxy-1,4-benzoquinone; and (c) monomethoxy-1, 4-hydroquinone. More particularly, the present invention discloses said active components in the following, approximate proportions: (a) 1% to 3%, (b) 2% to 4%, and (c) 0.5% to 1.5%; said proportions are a percentage of the total weight of the compound which composes the present invention. The disclosed process results in the deactivation of at least one ingredient reported to be an active component of grain concentrate: 2,6 dimethyl benzoquinone.

The compound is derived from wheat which is subjected to yeast fermentation, and becomes a medicine which is a source of biologically active substances. Most particularly, the present invention uses a solvent extraction, which is also known as partitioning fermented wheat germ extract method to produce a fermented wheat germ drug product.

The present invention differs from its closest prior art, a publication by Mate Hidvégi described below, even after the Hidvégi fraction was stripped of gluten by ethyl acetate extraction. A comparison between FIG. 2 (chromatogram of Hidvégi 250 Product after treatment with ethyl acetate to remove gluten) and FIG. 3 (the product of the present invention) are evidence of chemical differences between the two products. Similarly, a comparison between FIG. 4(A) (chromatogram of the Hidvégi 250 Product prior to gluten removal) and FIG. 4(B) (the product of the present invention) are evidence of chemical differences between the two products. Additionally, FIG. 1 demonstrates that the product produced by the present invention differs from the Hidvégi A250 Product in every quantifiable, physical characteristic other than taste: including gluten content, color, density, pH, appearance, and odor. More particularly, the present invention differs from Hidvégi because Hidvégi discloses the presence of an activated form of 2,6 dimethyl benzoquinone, whereas the present invention discloses a method for deactivating 2,6 dimethyl benzoquinone.

General Prior Art

Gluten is a protein composite which may be found in foods processed from wheat. Gluten constitutes more than 80% of the protein contained in wheat. About one percent of the people in developed nations have some intolerance to gluten, some of which can be severe enough to be life-threatening.

A gluten-free diet is medically accepted treatment for celiac disease, an autoimmune digestive ailment. Some people suffer from gluten intolerance, which is different from celiac in that it is not an immune mediated response. More commonplace is gluten sensitivity, which affects nearly 20 million people in the United States and is essentially a less severe form of gluten intolerance, In accordance with Section 206 of the Food Allergen Labeling and Consumer Protection Act of 2004, Title II of Pulp. 108-282, 118 Stat. 891, enacted Aug. 2, 2004 and 72 F.R. 2795-2817 the term gluten free is regulated to mean food products to those with less than 20 parts per million of gluten.

Gluten intolerance is an organism's inability to absorb gluten, a protein found in wheat, barley, oats and rye. Gliadins and glutenins are the two main components of the gluten fraction of the wheat seed. The production of anti-gliadin antibodies by an intolerant individual after the consumption of food containing gluten flattens out or damages the Villi of the small intestine, responsible for the absorption of nutrients, vitamins and trace elements. The result is that food particles leak into the bloodstream, and the body's natural defense system sees these particles as "foreign invaders." The problem becomes two-fold: the body cannot absorb important nutrients and the body seems to attack itself at the same time. In humans, the intolerance manifests in various forms in different individuals, including celiac disease, nonceliac gluten intolerance, dermatitis herpetiformis, migraines, and wheat allergy. The prevalence of disease associated gluten sensitivity has increased over the past 50 years and affects approximately 1% of the population [Rubio-Tapia et al. 2009; Fasano et al. 2003; Mustalahti et al. 2010].

Celiac disease is a type of more commonly manifested form of gluten intolerance. The symptoms and manifestations of celiac disease differ, very often, from case to case and depending on age of the affected individuals. Infants present gastrointestinal discomfort, diarrhea, often, bulky and particularly fetid defecation and immobility or loss of weight.

Children, besides the symptoms described above, may present nausea, vomiting, anorexia, anemia, dermatitis and mouth aphtha. They may present irritability as well. Adults, at the initial stage of the disease present a general feeling of sickness and fatigue, even when gastrointestinal disturbances are limited. Further, because of the limited absorption of vitamins, trace elements and nutrients, anemia, osteopenia, as well as neural and hormonal disorders are noted. Details about celiac disease can be found Fasano et al., 2003, "Prevalence of Celiac Disease in At-Risk and Not-At-Risk Groups in the United States: A Large Multicenter Study," Arch Intern Med. 163:286-292; Maki et al., 2003, "Prevalence of Celiac Disease among Children in Finland," The New England Journal of Medicine, 348:2517-2524; Sollid et al., 1989, "Evidence for a primary association of celiac disease to a particular HLA-DQ alpha/beta heterodimer," The Journal of Experimental Medicine, 169 (1): 345; Suanderline 1994, "Celiac Disease: a Review," Gastroenterology Nursing 17(3), 100-105; and Reifa and Lerner, 2004, "Tissue transglutaminase—the Key Player in Celiac Disease: a Review," Autoimmunity Reviews, 3(1): 40-45; each of which is hereby incorporated by reference in its entirety.

Although gluten intolerance-related diseases, such as celiac disease, are serious and often chronic diseases, they can be treated quite effectively, without medication or medical intervention. It is recommended amongst other things in the treatment of celiac disease, nonceliac gluten intolerance, dermatitis herpetiformis, migraines, and wheat allergy. The treatment is a strict life-long gluten-free diet, which results in the restoration of the small intestine wall in a normal condition and the control of the disease. Special attention should be given even to least gluten quantities because the degree of the lesion caused to the small intestine and the time of restoration are disproportional. This means eliminating virtually all foods made from these grains (e.g., food starch when it is prepared from wheat, and malt when it comes from barley). The gluten-free diet is a lifetime requirement. As such, a need exists for new gluten-free products.

Celiac disease (also known as gluten enteropathy or celiac sprue) is a disease in which inflammatory responses to the ingestion of gluten damage the proximal small intestinal mucosa and result in malabsorption of most nutrients. Gluten is hypothesized to stimulate an inappropriate T cell-mediated immune response in the intestinal submucosa that destroys mucosal enterocytes. (L. M. Tierney, Jr., S. J. McPhee, and M. A. Papadakis, eds. (2003), Current Medical Diagnosis & Treatment: 585-587). Characteristic symptoms of celiac disease include diarrhea, weight loss, abdominal distention, weakness, muscle wasting, growth retardation, and malnutrition. (L. M. Tierney, Jr., S. J. McPhee, and M. A. Papadakis, eds. (2003), Current Medical Diagnosis & Treatment: 585-587). Other symptoms that may occur even in the absence of the above symptoms, include fatigue, short statute, osteoporosis, dental enamel hypoplasia, and iron deficiency anemia. (L. M. Tierney, Jr., S. J. McPhee, and M. A. Papadakis, eds. (2003), Current Medical Diagnosis & Treatment: 585-587). Approximately 10% of celiac disease patients suffer neurological complications including ataxia and peripheral neuropathy. R. L. Chin, H. W. Sander, T. H. Brannagan, P. H. Green, A. P. Hays, A. Alaedini, N. Latov (2003), Celiac Neuropathy, Neurology, 60(10): 1581-1585). In addition, a cutaneous variant of celiac disease, dermatitis herpetiformis, exists. In this manifestation, patients suffer from a skin rash of pruritic papulovesicles over the extensor surfaces of the extremities, trunk, scalp, and neck. (L. M. Tierney, Jr., S. J. McPhee, and M. A. Papadakis, eds. (2003), Current Medical Diagnosis & Treatment: 585-587).

The prevalence of celiac disease in the United States is estimated to be I: 150 (M. Michael (2003), Recognizing and managing celiac disease in primary care, J. Am. Acad. Nurse Pract., 15(3): 108-114.), although whites of Northern European ancestry are afflicted at a higher rate than are those with African and Asian ancestry. (L. M. Tierney, Jr., S. J. McPhee, and M. A. Papadakis, eds. (2003), Current Medical Diagnosis & Treatment: 585-587).

To date, no medical treatment exists to eliminate the physiological response and consequent damage to intestinal mucosa following gluten ingestion. Thus, gluten sensitivities cannot be cured. Elimination of all gluten from the diet is essential. L. M. Tierney, Jr., S. J. McPhee, and M. A. Papadakis, eds. (2003), Current Medical Diagnosis & Treatment: 585-587). Thus, the only treatment available is compliance with a life-long gluten-free diet, which alleviates the symptoms of the disease and allows the intestinal mucosa to heal. (A. S. Abdulkarim and J. A. Murray (2003), The diagnosis of coeliac disease, Aliment. Pharmacol. Ther., 17(8): 987-95). Non-compliance with a gluten-free diet can result in recurrence of gastrointestinal symptoms, neuropathic symptoms, and/or other potentially life-threatening consequences.

Fermented Wheat Germ Extracts

The present invention allows the production of a gluten-free grain concentrate (GFGC), a substance suitable for use in foods, dietary supplements or medicaments. GFGC is more concentrated and easier to produce than incorporated in existing fermented wheat germ extract (FWGE), and providing a preferable substitute or alternative.

FWGE is made in several ways and said ways are described in previous patents. Research exists suggesting that FWGE supplements have anti-cancer and other medicinal benefits.

Analysis shows that FWGE is a polymolecular compound composed of thousands of molecules, and it can be shown that most of the material that makes up FWGE, and the majority of chemical entities do not contribute to anti-cancer effects. Several technologies can isolate fractions which appear to account for all of the anti-cancer benefits of FWGE, and separate out the non-active constituents.

The present invention discloses the simplest method with the least complicated and fewest number of steps, utilizing inexpensive technologies approved for use in the manufacture of food to create a substantially more concentrated, potent extract, with the highest concentration of active, anti-cancer constituents and least inactive constituents, compared with extracts which are made through existing technologies.

*Distinction from 2013 Hidvègi Patent

In particular, the first FWGE food supplement was taught by U.S. Pat. No. 8,563,050 B2 (Hidvégi) (the '050 patent). Currently, the most advanced FWGE food supplement, commonly known as A250. A250 requires the expensive freeze-dried FWGE as a starting point, and also requires multiple steps, including expensive solid-phase extraction technology. A250 is about 30 times more concentrated than FWGE made under the '050 patent. The method of the present invention produces GFGC, a food supplement which is about 70 times more concentrated than FWGE made by teaching of the '050 patent, and does so with fewer and less expensive steps.

Distinction from '474 Patent

Compared with FWGE food supplements taught by the '050 patent, and by U.S. Pat. No. 6,355,474 to Hidvégi et al. (the '474 patent), GFGC is a substance which is gluten free, dramatically more concentrated, and may be delivered in an equivalently bioactive dosage of approximately 80 to 500 mg formulated in accordance with the product of the present invention. By comparison, the conventional daily dose of FWGE is 5,500 mg per day.

The present invention discloses a product which tastes slightly sweet, and pleasant. The GFGC produced by the method of this disclosure thus overcomes the need for flavoring and additives to make existing FWGE food supplements palatable.

GFGC, according to the present invention, is stable at temperatures likely to be encountered during shipment via land and air-based delivery services, such as United Parcel Service (UPS) during warm-weather periods. Existing FWGE food supplements require the use of ice packs to maintain product integrity when the temperature of packages is liable to exceed 80 degrees Fahrenheit.

Existing FWGE food supplements are extremely hygroscopic, so that they absorb moisture readily. Absorption of moisture may spoil the product or require expensive handling and packaging to prevent said spoilage. The GFGC of the present invention is not hygroscopic, thus surmounting the shortcomings of the existing FWGE food supplements' hygroscopic propensities.

Due to the high necessary dosage, the unpleasant taste, hygroscopic and heat liable nature of existing FWGE substances, it has not been possible to blend them with other ingredients in a cost-effective manner to make beverages, health bars or fortified foods. The present invention discloses a method producing a GFGC product which overcomes these difficulties and allows the extract to be incorporated into beverages, bars and other foods. [00022] The methods of producing existing FWGE food supplements taught in the prior art differ from the method of producing GFGC food supplements as disclosed by the present invention. The prior art also teaches a ten to twenty-four-hour fermentation time, whereas GFGC according to the present invention optimally ferments in eight hours. In particular, the '474 patent includes several claims that do not apply to the present invention. Claim 1 of the '474 patent differs from the disclosure of the present invention because the present invention neither uses ground wheat germ nor does it boil off water and dry the fermented liquid.

Additionally, claim 2 of the '474 patent differs from the present invention in that the fermentation mixture is not subject to "continuous aerating." Claim 3 of the '474 patent differs from the present invention because the present invention does not use maltodextrin. Claim 4 of the '474 patent differs from the present invention because the present invention does not use auxiliary drying materials. Claim 5 of the '474 patent differs in that the present invention does not use boiling. Claim 6 of the '474 patent differs from GFGC, because the present invention does not use drying.

The '050 patent differs from the present invention in that the present invention does not add sweeteners or flavors, surfactants, auxiliary materials, does not lyophilize (see '050 patent, claim 1), nor does it add surface stabilizing, dispersing or emulsifying agents ('050 patent, claim 2); nor adds the surfactants listed ('050 patent, claim 3); nor adds lecithin ('050 patent, claim 4); nor does it add sweeteners or flavors ('050 patent, claims 5, 6 and 7).

The dose forms disclosed by '050 patent, claim 8, do not teach the liquid filled capsule form disclosed by the present invention. The current invention is favorably disposed to the use of liquid-filled capsules, suspensions and syrups as delivery mechanisms.

Claim 9 of the '050 patent teaches the use of a strain of *Saccharomyces cerevisiae* (baker's yeast). The present invention discloses the use of other organisms also, particularly, the bacteria used in sourdough bread.

Other Related Publications

The teaching associated with WO2010100515 (Hidvégi et al.) includes a reference to a biologically active fraction obtained from processed wheat germ, which fraction is similar to the biologically active fraction disclosed in the present invention. However, the present invention treats the fraction differently from WO2010100515. In particular, in WO2010100515 the product is obtained from A2, E, ES and L, whereas the UV chromatogram shows that the present invention's products differ from WO2010100515's A2, E, ES and L. While both the present invention and WO2010100515 use ethyl acetate as a solvent for their respective methods, WO2010100515 uses gel-filtration after the ethyl acetate extraction, but GFGC does not require it.

Fermented wheat germ has been shown to have beneficial properties. More particularly, a printed publication, by Yusuf, Oluwatosin K. and Justine T. Ekanem, "Studies of phytochemical constituents and anti-trypanosomal properties of fermented wheat germ and garlic bulbs extract on *Trypanosoma brucei*—infected rats." Journal of Medicinal Plants Research (4 Oct. 2010): 2016-2020 (hereinafter, "RI" or "Yusuf"). Fermented wheat germ as used in RI is not gluten free. In fact, page 2016 of RI states "Fermented wheat germ Extract called avemer [sic] was chosen for this work because it has been reported to. '. "Avemer" is a misspelling of Avemar (for example see AVEMAR Miss Spelling Domains site http://www.ipgeni.com/missspell/avemar (last visited 25 Apr. 2015).

According to the manufacture of Avemar, it "[c]ontains gluten" (see http://www.avemar.com.au/avemarinfo.news (last visited 25 Apr. 2015). The present invention does not contain gluten. In particular, the rule defining that a gluten free product must contain less than 20 mg/kg (see https://www.federalregister.gov/articles/2013/08/05/2013-18813/foodlabeling-gluten-free-labeling-of-foods (last visited 25 Apr. 2015). The present disclosure is gluten free. In particular, it has been measured to contain less than 5 mg/kg gluten, whereas Avemar has been measured to contain 121,000 mg/kg gluten.

Food products containing gluten are significantly different from gluten-free products. Some people are exceedingly sensitive to gluten, and must avoid gluten at all costs to avoid physical harm. Gluten sensitivity occurs in people who are intolerant to gluten, a protein found in wheat, barley, oats and rye. When ingesting foods containing gluten, they will develop gastrointestinal disorders including diarrhea, nausea, vomiting, bloating, nervous disorders such as headaches and fatigue, and hormone-system maladies leading to anemia, vitamin D deficiency and osteoporosis.

A diagnosis of Celiac disease is made when sufferers of gluten-sensitivity have measurable levels of antibodies to gliadin, a protein in gluten. It is theorized that anti-gliadin antibodies damage the Villi present in the small intestine (responsible for the absorption of vitamins, trace minerals and nutrients), leading to malabsorption. Damage to Villi can also allow food particles to leak into the bloodstream, a phenomenon referred to as "leaky gut syndrome." These particles can provoke the production of other anti-bodies and inflammatory immune response. Over the last fifty years the prevalence of disease associated gluten sensitivity has been increasing and affects approximately 1% of the population [Rubio-Tapia et al. 2009; Fasano et al. 2003; Mustalahti et al. 2010.]

Additional details about gluten sensitivity, Celiac and non-Celiac disease can be found at Molina-Infante J, et al., 2015, "Systematic review: noncoeliac gluten sensitivity" Aliment Pharmacol Ther., (9):807-20, Tovoli F, et al., 2014," Clinical and diagnostic aspects of gluten related disorders," World J Clin Cases, 16; 3(3):275-84, Mansueto P, et al., 2014 "Nonceliac gluten sensitivity: literature review," J Am Coll Nutr. 2014; 33(1):39-54, Fasano et al., 2003, "Prevalence of Celiac Disease in At-Risk and Not-At-Risk Groups in the United States: A Large Multicenter Study," Arch Intern Med. 163:286-292; Maki et al., 2003, "Prevalence of Celiac Disease among Children in Finland," The New England Journal of Medicine, 348:25172524; Sollid et al., 1989, "Evidence for a primary association of celiac disease to a particular HLA-DQ alpha/beta heterodimer," The Journal of Experimental Medicine, 169(1): 345; Suanderline 1994, "Celiac Disease: a Review," Gastroenterology Nursing 17(3), 100-105; and Reifa and Lerner, 2004, "Tissue transglutaminase—the Key Player in Celiac Disease: a Review," Autoimmunity Reviews, 3(1):40-45.

Diseases associated with gluten sensitivity are chronic and serious, and can be treated effectively by eliminating gluten containing foods from the diet. Adopting a strict, life time gluten-free diet can result in restoration of the small intestine cell wall and amelioration or reversal of other symptoms. The growing incidence of health problems associated with gluten ingestion, and the demonstrated success of maintaining a gluten-free diet in such patient, establishes the need for new gluten-free products.

Turning to other differences between the reference RI the present invention, Yusuf discloses the use of powdered wheat germ, whereas the current disclosure teaches the use of unground wheat germ. The present invention limits fermentation to eight hours or the product diminishes the active ingredient. Yusuf ferments the RI product for six times longer (48 hours), a period which would render the present invention inactive.

RI further discloses the extraction of paste as the product and discards all else. The present invention discards the paste product and uses what RI discards. As evidence, Yusuf discloses that RI users had to filter the extract before the evaporation. Additionally, the fermentation broth used in the present invention contains different components of the wheat germ than disclosed by RI. In particular, the present invention discloses that the product contains only the water-soluble part of the wheat germ concentrate.

RI further discloses a method which does not include a requirement for separation of the phases, which is a requirement of the present invention. The present invention teaches phase separation via centrifuge. Thus, the present invention teaches liquid-liquid extraction, whereas RI discloses an organic solvent extraction of the solids of the fermentation.

The Present Invention as a Drug

Consequently, the present invention is more effective at removing gluten, thereby making its benefits more widely available as a drug for gluten-intolerant and gluten-sensitive populations. In sum, FWGE has been shown to have many beneficial characteristics, including potent anticancer, anti-inflammatory, immune-modulatory, metabolic-regulatory, cardiovascular protective, and anti-aging properties. FWGE impairs critical aspects of the transformed phenotype, including aerobic glycolysis, the pentose phosphate pathway, and ribonucleotide reductase. It displays significant antiproliferative effects and triggers tumor cell death through apoptosis. Clinical data reveal significant benefits to patients from treatment with FWGE, including in combination with existing cancer therapies.

However, an existing drawback of FWGE is that it contains lectins (WGA, wheat germ agglutinin). Lectins are glycoproteins that bind to carbohydrates found in cell membranes damaging their function, leading to cell death. Lectin is poorly absorbed in the gut and is not toxic when ingested, but it causes agglutination of red blood cells once it reaches the blood stream in higher than nanomolar concentration, and is expected to be toxic if administered by injection, intravenously, intravenous and by methods that bypasses the gut. Therefore, FWGE containing lectins is expected to be toxic if administered by methods that come in contact with the blood.

Optimal routes of administration of any given drug can be influenced by many factors, drug pharmacokinetis (processes of uptake, distribution, and elimination of drugs), the location on a subject of drug application and the location drug tissue within the subject. Drugs which can be administered via multiple routes are more versatile, beneficial and valuable to patients, physicians and drug companies than drugs which suitable for limited routes of administration.

Routes of drug administration include topical, enteral, and parenteral routes. Topical drugs can be applied to the skin, the eyes, the ears and inhaled. Enteral administration involves any part of the gastrointestinal tract, by mouth (orally), many drugs as tablets, capsules, or drops, by gastric feeding tube, duodenal feeding tube, or gastrostomy. Parenteral administration includes intravenous (into a vein), intra-arterial (into an artery), intraosseous infusion (into the bone marrow), intra-muscular, intracerebral (into the brain parenchyma), intracerebro-ventricular (into cerebral ventricular system), intrathecal (an injection into the spinal canal) and subcutaneous (under the skin).

The presence of lectins/WGA render FWGE less suitable as an anticancer drug, particularly for injection or intravenous (IV) administration for individuals who cannot ingest even gluten-free FWGE substitute grain concentrate. Therefore, there is a need for a form of FWGE appropriate for alternative routes of administration other than through oral ingestion.

It was observed that the process of making a gluten-free grain-concentrate for fermented wheat germ drug product unexpectedly resulted in the removal of lectin. Therefore, the product produced by the method of this invention overcomes the drawbacks of grain concentrate substitute wheat germ drug products, with regard to alternative routes of administration other than through oral ingestion. Gluten-free grain-concentrate can be formulated for any route of administration: topical, enteral, and parenteral.

Distinction from 2012 Hidvégi Publication and Related A250 Product

The present invention has been compared to a fermented wheat germ concentrate taught by Mate Hidvégi in U.S. Pat. Publ. no. 2012/0164132 A1 (the "A250 Disclosure), the resulting product is referred to hereafter as "Hidvëgi A250 product". However, the present invention produces a compound which is both physically and chemically distinct from the Hidvégi A250 product.

The present invention uses the same starting material as the Hidvëgi A250 Disclosure, which is fermented wheat germ but said starting material is processed differently. As a result, the present invention does not contain gluten. The Hidvëgi A250 Disclosure does not have any data about gluten content. However, tests of the Hidvëgi A250 Product, a fermented wheat germ concentrate, show it does contain gluten. (See FIG. 1, first column.)

The presence (or conversely the absence) of gluten may result in markedly difference biological behavior. The present invention is WGA free (Wheat germ agglutinin—a protein that protects the wheat from insects). (See FIG. 1, first column.) Agglutinin and Gluten are not similar, and also have different biological effects.

The Hidvégi A250 Disclosure teaches how to produce the Hidvégi A25 Product, a material which contains glycosides of different flavonoids, while these components are completely missing from the gluten free product of the present invention.

The physical and chemical differences between the Hidvégi A250 Product, a material produced in accordance with the Hidvégi A250 Disclosure, and the material produced as a result of the present invention is due to the different processes taught by the two patents.

The method taught in the Hidvégi A250 Disclosure requires freeze-dried powder as starting material. This process denatures wheat proteins in many of the more than 20,000 types of proteins in the hexaploid species of plant of which wheat is one. The present invention does not employ freeze-drying, thus no protein denaturing. The freeze-drying requirement disclosed by Hidvégi prevents it from being used for, thus teaches away from using either the unconcentrated or concentrated broth as required by the present invention.

It has been suggested that if the Hidvégi A250 Disclosure teaches how to produce the Hidvégi A250 Product, a material that only differs from the present invention in that the Hidvégi A250 Disclosure teaches how to produce a material with gluten and the present invention does not. Consequently, to produce the product taught by the present invention, the suggestion is that one need only apply well known gluten removal techniques to the Hidvégi A250 Product, however this is not correct (compare FIG. 2 which is a chromatogram of the product of Hidvégi A250 Product after a well know gluten removal techniques was apply to the Hidvégi A250 Product with FIG. 3 a chromatogram of the product of the current invention).

The use of methanol and chloroform is one highly efficient gluten removal techniques. However, methanol is a highly toxic solvent, and chloroform is a carcinogen (https://www.ncbi.nlm.nih.gov/pmc/articles/PMC1637645/) The use of methanol is very limited in food production.

A similar effective removal technique is the use of diethyl ether. But diethyl ether is an extremely flammable hazardous solvent.

Ethyl acetate is a much safer solvent which is used for gluten removal, so the Ethyl acetate method is used in industrial scale production for gluten removal. Ethyl acetate is allowed to be used in drug production.

Thus, it has been suggested that if the Hidvégi A250 Product were treated with an ethyl acetate gluten removal technique, the result would be similar to or perhaps identical to the product resulting from the present invention.

Figure 1:
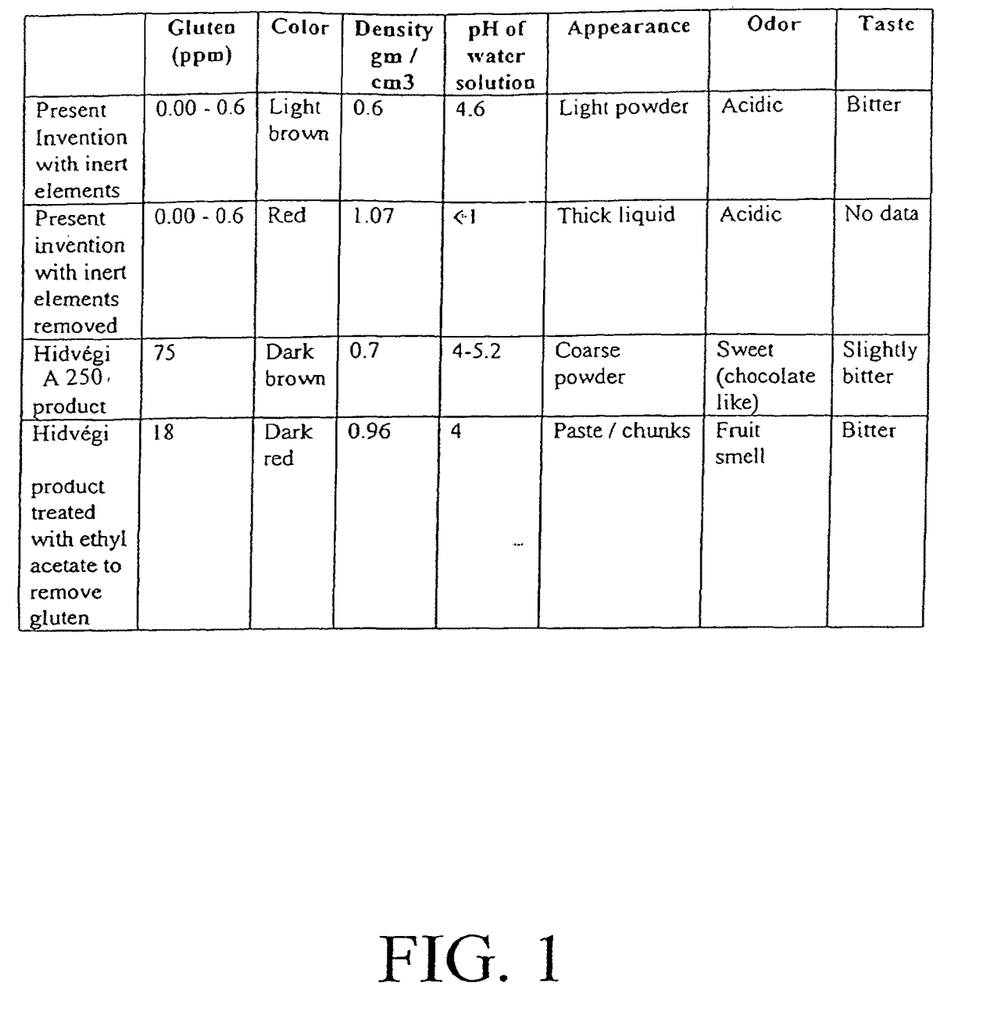
FIG. 1 is a table highlighting the quantifiable physical differences in the characteristics between and among the present invention, the Hidvégi A250 Product, and the Hidvégi A250 Product treated with ethyl acetate to remove gluten.

FIG. 1 is a table distinguishing the product produced by the present invention from the Hidvégi A250 Product with gluten and without gluten. The present invention has particular quantifiable, physical characteristics including gluten content, color, density, pH, appearance, odor and taste. Said characteristics are enumerated on lines 1 and 2 of FIG. 1. Line 1 details the present invention with inert elements. Line 2 details the present invention with inert elements removed.

Figure 3:
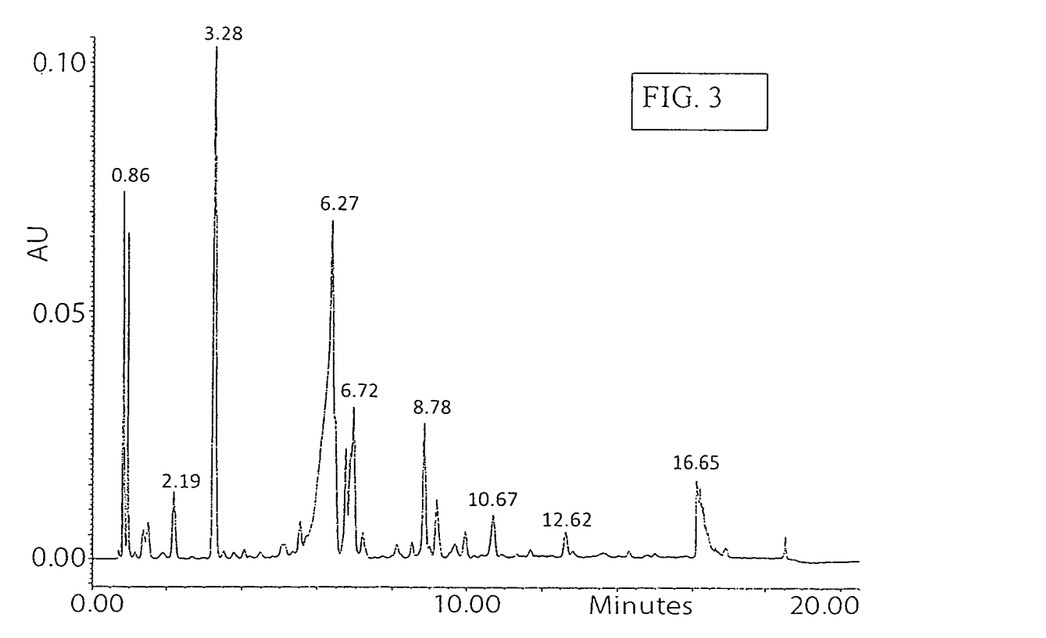
FIG. 3 is a chromatogram of the product of the present invention.

The present invention has quantifiable chemical characteristics. FIG. 3 displays said characteristics of the present invention in the form of a chromatogram.

Returning to FIG. 1, the Hidvégi A250 Product also has particular quantifiable, physical characteristics including gluten content, color, density, pH, appearance, odor and taste. Said characteristics appear on Line 3 of FIG. 1. Line 4 depicts these characteristics following removal of gluten from the Hidvégi A250 Product.

Figure 4A:
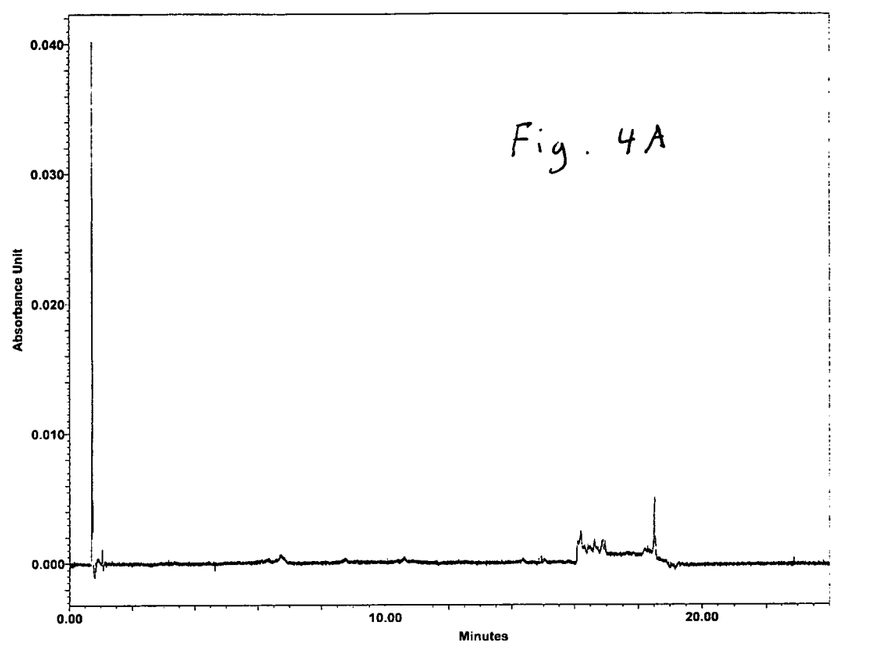
FIG. 4 are chromatograms of the paste extract of the Hidvégi A250 Product prior to removing gluten (graph "A"), and of the current invention (graph "B"), placed together in FIG. 4 to facilitate comparison.
Figure 4B:
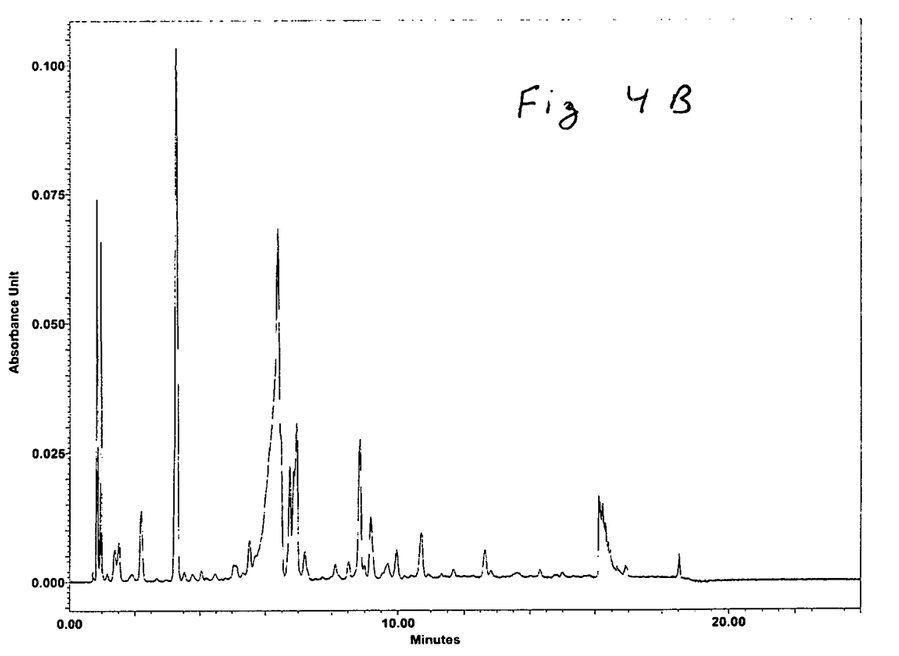

The Hidvégi A250 Product has quantifiable chemical characteristics. FIG. 4 compares the chemical characteristics of the Hidvégi A250 Product; 4(A) is a chromatogram depicting the Hidvégi A250 Product before the gluten is removed; 4B is the product of the present invention.

Figure 5:
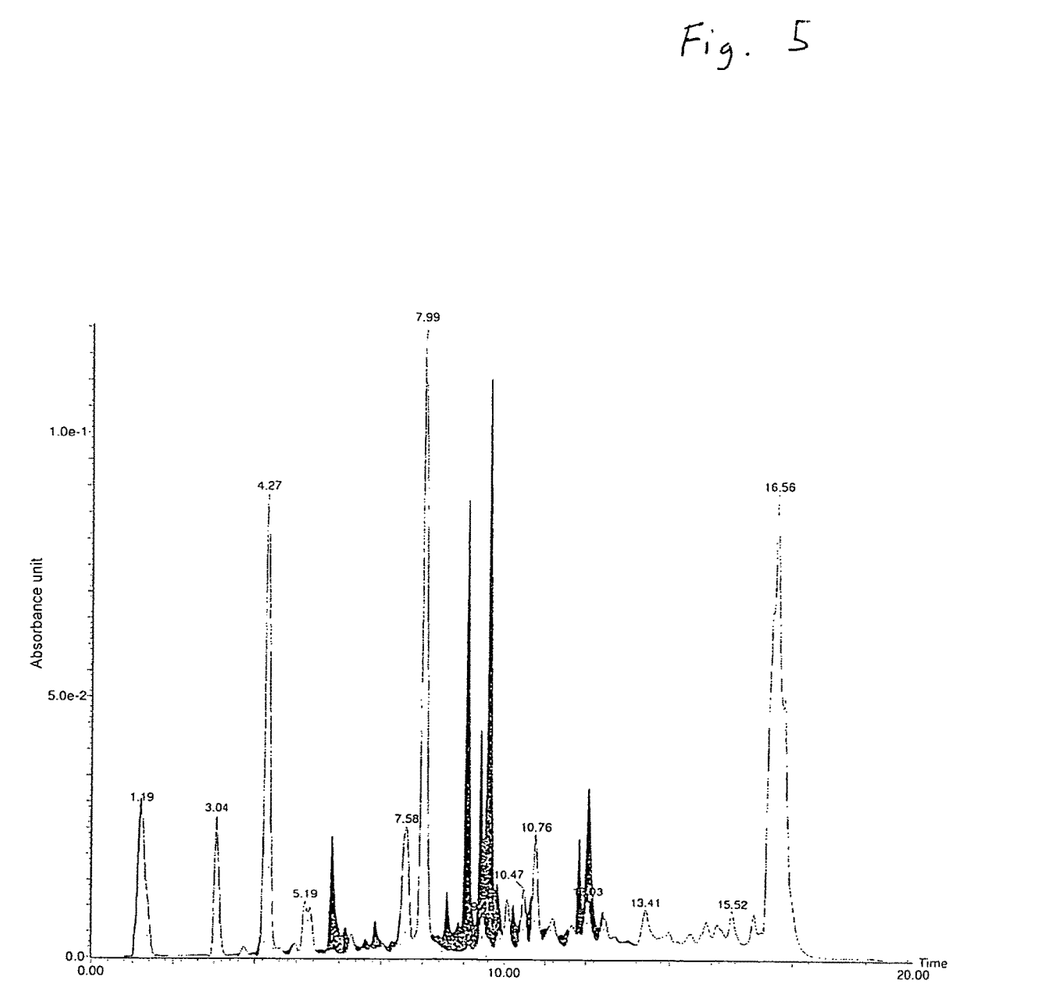
FIG. 5 is an overlay of two chromatograms of the Hidvégi 250 Product dissolved in distilled water before and after the solution was extracted with ethyl acetate to remove gluten. The darker pattern is the Hidvégi 250 Product containing gluten. The lighter pattern is the Hidvégi 250 Product dissolved after gluten was removed with ethyl acetate; the lighter peaks correspond to the chromatograph of the Hidvégi 250 Product shown in FIG. 2.

FIG. 5 is a chromatogram depicting the Hidvégi A250 Product dissolved in distilled water and the solution extracted with ethyl acetate to remove gluten. The chromatogram of FIG. 5 overlays the two resulting subfractions. The darker peaks or patterns evidence chemical characteristics of the Hidvégi A250 Product. The lighter peaks evidence the gluten free result after ethyl acetate extraction, and are the same as shown in FIG. 2.

Figure 2:
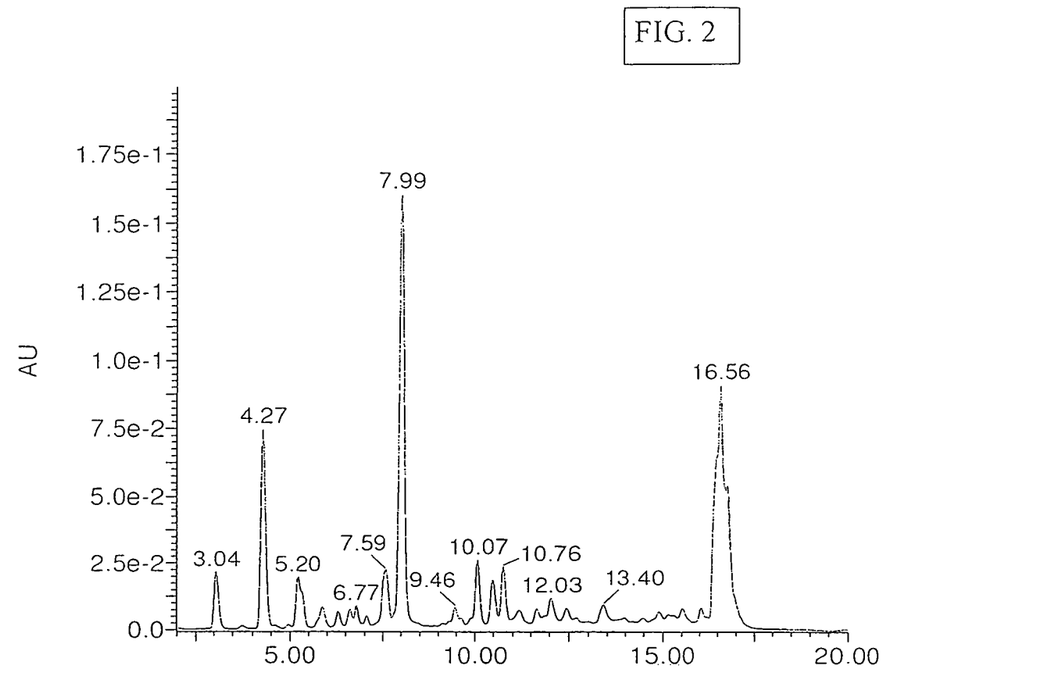
FIG. 2 is a chromatogram of the Hidvégi A250 Product after treatment with ethyl acetate to remove gluten.

Referring to FIG. 2, the chromatogram shows the Hidvégi A250 Product after treatment with ethyl acetate to remove gluten executed on the same machinery as the FIG. 3 chromatogram of the product of the current invention.

In sum, a comparison between FIG. 2 (chromatogram of Hidvégi 250 Product after treatment with ethyl acetate to remove gluten) and FIG. 3 (the product of the present invention) are evidence of chemical differences between the two products. Similarly, a comparison between FIG. 4(A) (chromatogram of the Hidvégi 250 Product prior to gluten removal) and FIG. 4(B) (the product of the present invention) are evidence of chemical differences between the two products.

Additionally, FIG. 1 demonstrates that the product produced by the present invention differs from the Hidvégi A250 Product in every quantifiable, physical characteristic other than taste: including gluten content, color, density, pH, appearance, and odor.

The Yusuf publication also teaches the use of ethyl acetate to remove gluten from wheat germ products. The application of said Yusuf ethyl acetate gluten removal technique to the material produced using the Hidvégi A250 Disclosure produces a very different product than the product associated with the present invention. Evidence of said difference can be seen by comparing the chromatograms of the present invention with the chromatograms of Yusuf ethyl acetate gluten removal technique to Hidvégi A250 Product.

Row et al. (Biores. Technol. 2006. 97: 790-793) (the "Row publication") also teaches the use of ethyl acetate to remove gluten from wheat germ products. The application of said Row ethyl acetate gluten removal technique to the Hidvégi A250 Product also products a very different product than the product associated with the present invention. Evidence of said difference can be seen by comparing the chromatograms of the present invention with the chromatograms of Row ethyl acetate gluten removal technique to the Hidvégi A250 Product.

While both Yusuf and Row teach the use of ethyl acetate to remove gluten from wheat germ products, they do not teach the use of ethyl acetate extraction to remove gluten from fermented wheat germ extract. The use of ethyl acetate extraction to remove gluten from fermented wheat germ extract is not taught because it denatures some of the proteins in fermented wheat germ extract.

The Hidvégi A250 Disclosure teaches how to produce a material but does not eliminate gluten from said material because to do so which denature the proteins which were identified as the active ingredient. In particular, the Hidvégi A250 Product was treated with the most common method of removing gluten and the result was an inactive product. In particular, the regular way of making gluten free flour was used on the Hidvégi A250 Product. More particularly, the regular way of making gluten free flour, is to boil the suspension at high temperature and dissolve the starch with cold water. It was found that boiling the Hidvégi A250 Product significantly reduces its activity. Thus, it may be concluded that the method can't be used to eliminate or reduce the gluten from the Hidvégi A250 Product.

It was hypothesized that the extract described by Yusuf in 2010 is similar to our gluten free extract made from the clarified fermentation broth, and to test this hypothesis a High-Performance Liquid Chromatography (HPLC) test was prepared to disprove that the two extracts are different.

Yusuf's paper describes a method in which the wheat germ was fermented with Baker's yeast and the paste was extracted with ethyl acetate. Although the meaning of the paste is not properly described, based on the properties of the different stages of FWGE production the mixture of wheat germ, yeast and water is most likely the paste that is mentioned in the paper.

Sample preparation:

Wheat germ was fermented with Baker's yeast overnight and the paste was extracted with organic solvent in 1:1 ratio, as it was described by Yusuf in 2010. The mixture was vortexed and the phases were separated at 12,000 rpm. The upper phase was dried under vacuum at 50 C overnight. The sample was mostly oil, with reddish color (Sample PI).

20 mg of the dried sample was dissolved in 500 uL of methanol, and 25 uL of the solution was further diluted with distilled water. The final concentration of the sample was 1 mg/mL, and 20 uL was injected into a HPLC system. The diode array detector was set to 200400 nm detecting range, and the chromatogram was exported at 280 nm.

Sample 0217-1 was prepared by diluting 15 mg of FWGE-SCP in 300 uL Methanol. The sample was homogenized and suspended with vortex and sonication. The sample was separated from the excipients with centrifuge at 12,000 rpm. 200 uL of the supernatant was transferred into a separate PCR tube and was dried under vacuum at 50 C. The dry sample was dissolved with DMSO and diluted with distilled water to 1 mL. 20 uL was injected into a HPLC system. The diode array detector was set to 200-400 nm detecting range, and the chromatograms were exported at 280 nm.

Results

Both of the samples were injected in the same concentration into the HPLC system. The chromatograms appear to be very different. While Sample 0217-1 has many UV active components between 2 min and 16 min retention, the paste extract has only some UV active components, and mostly after 16 min. (FIG. 4).

CONCLUSION

Extracting the very crude paste results in a much more complex compound. The presence of yeast cells and especially the different lipid components of wheat germ in the unprocessed paste significantly changes the composition of the final product, reducing the abundance of the UV active components of the extract.

The test failed to disprove that the two extracts are different, so that the claim that FWGE-SCP is different from the extract published by Yusuf et al. in 2010, is still presumed to be correct.

SUMMARY OF THE INVENTION

The present invention is a gluten-free, fermented wheat germ drug product and method of preparation necessary to make said fermented wheat germ drug product. Disclosed is a product with at least three active components including (a) 2,6-dimethoxy-1,4-hydroquinone; (b) monomethoxy-1,4-benzoquinone; and (c) monomethoxy-1,4-hydroquinone. More particularly, the present invention discloses said active components in the following approximate proportions: (a) 1% to 3%, (b) 2% to 4%, and (c) 0.5% to 1.5%; said proportions being a percentage of the total weight of the compound which composes the present invention.

The present invention's process of iteratively exposing the materials to heating and mechanical manipulation, appears to result in the deactivation of the 2,6 dimethyl benzoquinone component. The precise mechanism by which this occurs is uncertain.

The basis for the disclosure that 2-6 methoxy substituted benzoquinones is not an active component of the present invention is vivo experiments. In particular, when the 2-6 methoxy substituted benzoquinones the activity level of the present invention remained unchanged. Whereas, when any of a b c were removed the activity level of the present invention decreased.

It should also be noted there a difference in granularity between the present invention and an alternative method of producing a related food patent. Said material granularity is a measure of the conglomeration of discrete solid, macroscopic element of a compound. Because the present invention is more granular than the food related patent, the present invention has a smaller particle size, which makes them more cohesive and more easily and faster to suspended in a liquid.

The product of this invention is a drug can be formulated in to capsules, tablets, granules, sachets, suspensions, emulsions, sprays, suppositories, ointments, or patches with the addition of auxiliary materials and procedures commonly used in dietary supplement and pharmaceutical technology, and formulated in to fortified beverages, food bars and foods, with the addition of auxiliary materials and procedures commonly used in beverage, health bar and drug technology.

DESCRIPTION OF THE DRAWINGS

It is helpful to note that a comparison between FIG. 2 (chromatogram of Hidvégi 250 Product after treatment with ethyl acetate to remove gluten) and FIG. 3 (the product of the present invention) are evidence of chemical differences between the two products.

It is also helpful to note that the comparison between FIG. 4(A) (chromatogram of the Hidvégi 250 Product prior to gluten removal) and FIG. 4(B) (the product of the present invention) are evidence of chemical differences between the two products.

DETAILED DESCRIPTION OF THE INVENTION

GFGC may be formulated by a number of different methods. The preferred method is a function of the form of the GFGC desired. In particular, the GFGC forms include a solid, a liquid and suspension of solid and liquid. The first method of preparing GFGC is described as follows:

The invention is the product of the following method used to make our gluten free fermented wheat germ extract:

heating 400 gallons of filtered water to a temperature of 25 C;

adding said water to a vessel containing 100 lbs. of crumbled baker's yeast (Saccharomyces cerevisiae);

mixing said yeast water mix constantly for 1 hour;

adding 1,000 lbs. of raw wheat germ to said yeast water mix;

mixing said wheat germ yeast water mix for 9 to 12 hours, allowing temperature to raise to a temperature of not more than 46 C;

decanting said wheat germ yeast water mix through a liquid-solid separator with a 100- to 150-micron screen into a stacked disc centrifuge;

operating said stacked disc centrifuge to remove at least 85% of the yeast from said low wheat germ liquid forming a low yeast liquid;

transferring said low yeast liquid to a plate and frame filtration device with 1 to 3-micron filter plates;

operating said plate and frame filtration device to produce clarified broth no more than 7% dissolved solids;

transferring said broth to a vacuum evaporator;

operating said vacuum evaporator to remove water from said broth producing a concentrated broth which has no less than 30% dissolved solids;

transferring said concentrated broth to a second centrifuge;

operating said second centrifuge to remove remaining suspended solids forming a clarified broth;

transferring said clarified broth solid to a third vessel containing sufficient ethyl acetate to remove at least 99.9% of gluten from said clarified broth forming an ethyl acetate liquid layer and a water layer;

decanting said ethyl acetate liquid layer from said third vessel into a fourth vessel;

evaporating said ethyl acetate liquid in said forth vessel forming concentrated ethyl acetate liquid which contain at least 6% solids;

mixing equal amounts of microcrystalline cellulose and hydroxypropyl methylcellulose in sufficient quantities forming a cellulose mix which has a volume of nine times the volume of said concentrated ethyl acetate liquid;

adding said cellulose mix to said concentrated ethyl acetate liquid in said fourth vessel forming final mix;

pouring said final mix into a vacuum paddle dryer;

setting said vacuum paddle dryer to operate with a vacuum of 26.5 inches to 27.5 inches of mercury, a temperature of 30 C-50 C and a 10-50 rpm drum rotation speed;

operating said vacuum paddle dryer for up to 24 hours using said vacuum, heat and drum rotation speed setting forming stable dry powder.

It should be noted that the order of combining the clarified broth and ethyl acetate is very important. If the clarified broth is added to the ethyl acetate in accordance with the method, the process will proceed. However, if the ethyl acetate is poured into the clarified broth not in accordance with the method, then a substance with a mayonnaise-like appearance could form, rendering the result unusable.

An alternate method is to create GFGC broth by combining one part baker's yeast, three parts of raw wheat germ and thirty-two parts water.

Mix slowly for eight to 18 hours at 30° C. to 40° C., decant and separate wheat germ and yeast (or bacteria) from broth with a centrifuge.

Filter broth, first with a 5-micron filter or larger, and second with a 0.2-micron filter.

Concentrate broth with a falling film evaporator or similar method to 10% to 20% solids.

Standardize the pH of the broth at 2. In the preferred method and embodiment, the standardizing agent is phosphoric or hydrochloric acid.

Wash with a food grade volatile non-polar liquid. Ethyl acetate is preferred.

Combine a volume of concentrated broth with half as much ethyl acetate, mix and separate with centrifuge, will result in "Upper Layer" (clear dark reddish, ethyl acetate), a thin "Solid Layer" (light brown), "Bottom Layer (clear, dark brown, water), and pellet.

Optionally, instead of producing a solvent-free state, after removing approximately between 90% and 95% of ethyl acetate—a mixture of not less than 80% ethanol and not more than 20% glycerol is added. The volume of said mixture should be about with the volume of the remaining ethyl acetate, then mixed thoroughly. With further distillation the rest of the ethyl acetate and ethanol is removed and leaving the glycerol. The distillate temperature should not exceed 50° C., preferably 40° C.

Recover Upper Layer (this has the active ingredient we are looking to recover) avoiding thin Solid Layer as much as possible, draw off Bottom Layer (avoiding thin Solid Layer), add an amount of ethyl acetate equal to half the volume of the Bottom Layer.

Repeat separation. Repeat as necessary, but it is believed that 50% of material is recovered in the first wash, 30% is recovered in the second wash, 15% in the third wash, and so on, so depending to the cost of the process, we may choose to stop this procedure at 2 or 5 washes.

Combine recovered "Upper Layer" portions from each wash, filter if necessary, to achieve clear liquid. Reduce (boil off) ethyl acetate and recover, until a solvent free state is reached. A dark solid will remain, the active ingredient. To prevent the solid extract from adhering to the bottom of the evaporation vessel, when approx. 80% of the solvent is removed, add methylcellulose and silica in equal proportion, in an amount equal to the estimate amount of recovered solid.

It is estimated that 1% of solids will be recovered from a volume of concentrated broth, with inert ingredients, preferably equal amounts of methylcellulose and silica. Additionally, immiscible liquids such as propylene glycol, heptane or hexane, may be used in place of the solid methylcellulose and silica agents. The recovered dark powder will be 2% of the concentrated broth. If a liquid final product is desired, as the ethyl acetate is reduced, when approx. 80% is removed, add propylene glycol, and continue boiling off ethyl acetate. Either of these GFGC products are known as GFGC-I In a preferred method, the above steps are followed through instead of adding a mixture of not less than 80% ethanol and not more than 20% glycerol. In lieu of ethanol/glycerol and subsequent steps, most but not all of the ethyl acetate is evaporated off with heat, leaving a residue of GFGC in solution with ethyl acetate, water and acids (GFGCS). The acid or acids are those produced as a result of the fermentation process and may vary depending upon the initial wheat germ raw material. The GFGC and GFGCS are present in a ratio of between approximately 1 and 1:50. To prevent deactivation of GFGC the GFGCS should not be exposed to temperatures in excess of 50° C., and preferably 40° C.

The remaining GFGC solids must be estimated. The preferred estimating method includes taking 10 grams of GFGCS and heating the sample to not more than 50° C., and optimally 40° C., under a vacuum until only solid material remains. Then the solid materials are weighed to determine a ratio of GFGC to GFGCS. The weight of the GFGCS is multiplied by the ratio to determine the mass of the GFGC. For example, if the GFGCS weighs 100 grams and a 10-gram sample was removed, and the 10-gram sample yielded one gram of GFGC, then the GFGC would be calculated by dividing the one-gram resultant by the 10-gram example and multiplying it by the remaining 90 grams of GFGCS, giving 9 grams of GFGC. The 9-gram result is used to calculate the volume of excipients in the next step.

The GFGCS is then combined with excipients in a ratio of approximately 1:9 of the estimated solids to the excipient (GFGCSE). The foregoing example of 9 grams of GFGC solids, would dictate 81 grams of excipients. The preferable excipients are hydroxypropyl methylcellulose (a/k/a hypromellose, HPMC) and microcrystalline cellulose (MCC) in a preferred ratio of 6.1 HPMC to 4.0 MCC, or approximately 3:2.

Optionally, prior to combining the GFGCS with excipients, a salt, preferably a food-grade inorganic salt such as $MgSO_4$ is added to the GFGCS in a proportion of up to of the mass of GFGCS to facilitate reduction of water in the solution. The mixture is stirred for approximately five minutes and left to settle to the bottom. The liquid is decanted after two to eight hours. At this time the excipients are added to the dewatered mixture resulting in a GFGCSE with reduced clumping of the excipients in order to produce a more uniform end product.

GFGCSE is then transferred to a paddle dryer. The paddle dryer is run, under a vacuum preferably starting at 24½ inches mercury, at product temperatures of preferably 40° C., not higher than 50° C. During the approximately 2 h treatment time the vacuum is gradually increased to 29% inches of mercury. The product of this step is termed GFGCP.

The GFGCP is milled into a fine powder (GFGCFP) using a Hammer Mill or similar apparatus. The GFGCFP is transferred to a paddle dryer or a fluid-bed dryer to remove trace ethyl acetate, residual water and acids at temperatures of preferably 40° C. but not higher than 50° C., for approximately two hours or until the moisture is reduced to 3% to water content by weight. Optionally this step may be accelerated by using warm nitrogen gas at no more than 50° C., or a partial vacuum of between 24% and 29% inches of mercury. The result of this step is GFGC-2.

Confirm the identity of GFGC with High Performance Liquid Chromatography (HPLC). The liquid GFGC-I product which results from the first method utilizing ethanol/glycerol solution, proportionately has the same biological effect as the whole FWGE from which it was recovered, but the product of that method can be utilized at a dosage which can be as much as 50 times lower than the dosage required for whole FWGE. The GFGC-2 product resulting from the option method can be utilized at a dosage at least 10 times lower than whole FWGE. The product from this method has no unpleasant flavor, unlike whole FWGE, is not hygroscopic, like whole FWGE, is not sensitive to degrade in temperatures above, like whole FWGE, and can be administered orally, and by IV, unlike whole FWGE which can only be administered orally.

The GFGC resulting from said method of production has the following characteristics, including:

1. Soluble in water,
2. Soluble in dimethyl sulfoxide (DMSO),
3. Soluble in ethyl acetate,
4. Essentially free of lectins,
5. Essentially free of flavonoids,
6. Characteristic high-performance liquid chromatography (HPLC, sometimes referred to as "high pressure liquid chromatography") signature,
7. Not hygroscopic,
8. Easily compounded with other compounds,
9. Chemically stable from 0° C. to 50° C. (for long shelf life).

For laboratory purposes, the following procedure is the preferred embodiment of GFGC.

In an opened vessel add 75-150 grams of unground wheat germ to 700-800 milliliters of filtered water. Within an hour add 15-30 grams of *Saccharomyces cerevisiae*—commonly known as baker's yeast or, alternatively, a sourdough yeast such as *Saccharomyces exiguous, Kazachstania exigua* or a *Candida* variety. The mixture of wheat germ, yeast and water is continuously stirred without any additional aeration at 25°–40° C., optimally for 8-10 hours. After the fermentation is completed, the insoluble parts of the starting materials are separated with 5-15 micron filtration. The filtered water solution is concentrated by distillation at 40° C. to 20-30% mass-to-volume Following the completion of the concentration process an amount of organic solvent—for example ethyl-acetate—equal to the amount of concentrate is added to the concentrate. Stir them gently for 15-30 minutes. Use a centrifuge to separate the two phases.

After separating the organic, less dense layer—which should be about 50% of the total volume—remove the organic layer and place the organic layer in a dryer or reaction vessel. Heat at no more than 40° C. until all of the liquid is removed.

For industrial purposes, the following method is preferred. The purification process steps (prior to vacuum evaporation), starting with completed (whole) fermentation broth, are as follows:

1. Whole/final broth is fed to a vibrating sieve (80-mesh screen) to remove the bulk of the wheat germ grains. The overflow is directed to a screw press containing 2 additional screens to further dewater the waste solids and perhaps permit recycle of pressed broth for possible increased actives yield.
2. The sieved broth is fed to a stacked-disk centrifuge to further remove insoluble solids and the majority of the yeast. The clarified broth (a/k/a supernatant) is prepared for the next filtration step.
3. The filter press, consisting of fifty (50) 30"×30" plates and frames, is prepared by installing individual filter paper between each plate and frame after which the plates/frame/paper are hydraulically compressed. Other filtration technology could be used here such as a pressure-leaf filter or a basket centrifuge. Approximately 200 liters of water and 50 lbs. of filter aid (Celite or Celatom) of a grade range (e.g., Celatom's FP-4) are mixed/slurried for a pre-coat and fed to the filter press to establish an initial filter cake bed.
4. Filter aid is also added (as a body feed) and mixed with the centrifuged supernatant broth at a dosage of 0.5-1.5% by weight. The slurried mixture is fed to the pre-coated filter press to remove the majority of insoluble solids.
5. The filter press filtrate is polished-filtered using a 1.0-micron filter cartridge(s) and a 0.22- or 0.45-micron filter cartridge(s) to significantly reduce the bioburden prior to vacuum evaporation.

We claim:

1. A gluten free grain concentrate produced from only water soluble concentrate, without maltodextrin, auxiliary drying material, drying fermented liquid or boiling off water, comprising 2,6-dimethoxy-1,4-hydroquinone; monomethoxy-1,4-benzoquinone; and monomethoxy-1,4-hydroquinone; prepared by three phased temperature controlled process comprising the steps of:

(A) a fermentation process comprising:
  a) heating 400 gallons of filtered water to a temperature of 25 C;
  b) adding said water to a vessel containing 100 lbs of crumbled baker's yeast (*Saccharomyces cerevisiae*);
  c) mixing said yeast water mix constantly for 1 hour;
  d) adding 1,000 lbs of raw wheat germ to said yeast water mix;
  e) continuously stirring said wheat germ yeast water mix for 8 to 10 hours without additional aeration allowing temperature to raise to a temperature of not more than 40 C;

(B) an active-ingredient extraction process comprising:
  f) decanting said wheat germ yeast water mix through a liquid-solid separator with a 100 to 150-micron screen into a stacked disc centrifuge to initiate liquid-liquid extraction;
  g) operating said stacked disc centrifuge to remove a yeast paste consisting of at least 75% of the yeast from said low wheat germ liquid forming a low yeast liquid, and discarding said yeast paste;
    wherein said low yeast liquid contains only water soluble portion of said wheat germ concentrate;
  h) transferring said low yeast liquid to a plate and frame filtration device with filter plates having one to five-micron openings; operating said plate and frame filtration device to produce a clarified broth no more than 7% dissolved solids;
  i) transferring said broth to a vacuum evaporator;
  k) operating said vacuum evaporator to remove water from said broth producing a concentrated broth which has no less than 28% dissolved solids;
  l) transferring said concentrated broth to a second centrifuge;
  m) operating said second centrifuge to remove remaining suspended solids forming a clarified broth;
  n) transferring said clarified broth solid to a third vessel containing sufficient ethyl acetate to remove at least 99.4% of gluten from said clarified broth forming an ethyl acetate liquid layer and a water layer;
  o) decanting said ethyl acetate liquid layer from said third vessel into a fourth vessel;
  p) evaporating said ethyl acetate liquid in said forth fourth vessel forming concentrated ethyl acetate liquid which contain at least 6% solids;
  q) mixing equal amounts of microcrystalline cellulose and hydroxypropyl methylcellulose in sufficient quantities forming a cellulose mix which has a volume of nine times the volume of said concentrated ethyl acetate liquid;
  r) adding said cellulose mix to said concentrated ethyl acetate liquid in said fourth vessel forming final mix;

(C) a liquid-to-solid transformation process comprising:
  s) pouring said final mix into a vacuum paddle dryer;
  t) setting said vacuum paddle dryer to operate with a vacuum of 26 inches to 28 inches of mercury, a temperature of 30 C-60 C and a 3-60 rpm drum rotation speed;
  u) continuously stirring said final mix with said vacuum paddle dryer for up to 24 hours using said vacuum, heat and drum rotation speed setting forming stable dry powder;
    wherein said three processes require about 72 hours continuously, said 72 hours being comprised of approximately 24 hours of said fermentation process, 24 hours of said active-ingredient extraction process, and approximately 24 hours of drying said liquid-to-solid transformation process.

2. The gluten free grain concentrate of claim 1 wherein said drum rotation speed is 10-50 rpm.

* * * * *